(12) United States Patent
Hviid

(10) Patent No.: US 11,871,172 B2
(45) Date of Patent: *Jan. 9, 2024

(54) STAND-ALONE MULTIFUNCTIONAL EARPHONE FOR SPORTS ACTIVITIES

(71) Applicant: BRAGI GmbH, Munich (DE)

(72) Inventor: Nikolaj Hviid, Munich (DE)

(73) Assignee: BRAGI GMBH, Munich (DE)

( * ) Notice: Subject to any disclaimer, the term of this patent is extended or adjusted under 35 U.S.C. 154(b) by 251 days.

This patent is subject to a terminal disclaimer.

(21) Appl. No.: 17/104,542

(22) Filed: Nov. 25, 2020

(65) Prior Publication Data

US 2021/0084403 A1    Mar. 18, 2021

Related U.S. Application Data

(63) Continuation of application No. 15/113,435, filed as application No. PCT/EP2015/051356 on Jan. 23, 2015, now Pat. No. 10,856,063.

(30) Foreign Application Priority Data

Jan. 24, 2014 (DE) ..................... 10 2014 100 824.3

(51) Int. Cl.
| | |
|---|---|
| *H04R 1/10* | (2006.01) |
| *A61B 5/1455* | (2006.01) |
| *A61B 5/00* | (2006.01) |
| *G06F 3/01* | (2006.01) |
| *G06F 3/044* | (2006.01) |
| *H04R 5/033* | (2006.01) |

(52) U.S. Cl.
CPC ....... *H04R 1/1041* (2013.01); *A61B 5/14551* (2013.01); *A61B 5/6817* (2013.01);
(Continued)

(58) Field of Classification Search
CPC .. H04R 1/1041; H04R 1/1016; H04R 1/1058; H04R 1/1083; H04R 5/033;
(Continued)

(56) References Cited

U.S. PATENT DOCUMENTS

| | | |
|---|---|---|
| 2005/0027537 A1 | 2/2005 | Krause et al. |
| 2007/0003098 A1 | 1/2007 | Martenson et al. |
| (Continued) | | |

FOREIGN PATENT DOCUMENTS

| | | |
|---|---|---|
| CN | 101919261 A | 12/2010 |
| CN | 103475971 A | 12/2013 |
| (Continued) | | |

OTHER PUBLICATIONS

"State Intellectual Property Office of The People's Republic of China", Application No. 201580014977.1, first office action dated Sep. 4, 2018, 9 pages.

(Continued)

*Primary Examiner* — Eric F Winakur
*Assistant Examiner* — Abid A Mustansir
(74) *Attorney, Agent, or Firm* — Goodhue, Coleman & Owens, P.C.

(57) ABSTRACT

An apparatus is described which comprises the following: (a) a housing configured to be carried in an ear, (b) a motion sensor unit for acquiring motion data, (c) a physiological sensor unit for acquiring physiological data, (d) a data processing unit configured to generate performance data based on the motion data and/or the physiological data, (e) a signal processing unit configured to generate an audio signal based on the generated performance data, and (f) a loudspeaker for outputting the generated audio signal, wherein the motion sensor unit, the physiological sensor unit, the loudspeaker, the data processing unit, and the signal processing unit are incorporated in the housing. Furthermore, a system, a method and a use is described.

17 Claims, 3 Drawing Sheets

(52) U.S. Cl.
CPC .............. *G06F 3/017* (2013.01); *G06F 3/044* (2013.01); *H04R 1/1016* (2013.01); *H04R 1/1058* (2013.01); *H04R 1/1083* (2013.01); *A61B 5/6843* (2013.01); *A61B 2562/0219* (2013.01); *H04R 5/033* (2013.01); *H04R 2420/07* (2013.01); *H04R 2460/13* (2013.01)

(58) Field of Classification Search
CPC .. H04R 2420/07; H04R 2460/13; H04R 1/14; H04R 1/1091; H04R 2201/107; A61B 5/14551; A61B 5/369; A61B 5/6817; A61B 2562/0219; G06F 3/017; G06F 3/044
See application file for complete search history.

(56) References Cited

U.S. PATENT DOCUMENTS

| | | |
|---|---|---|
| 2008/0076972 A1 | 3/2008 | Dorogusker et al. |
| 2008/0146892 A1 | 6/2008 | LeBoeuf et al. |
| 2008/0255430 A1 | 10/2008 | Alexandersson et al. |
| 2009/0097689 A1 | 4/2009 | Prest et al. |
| 2009/0105548 A1 | 4/2009 | Bart |
| 2009/0177097 A1 | 7/2009 | Ma et al. |
| 2010/0086144 A1 | 4/2010 | Sibbald |
| 2013/0131519 A1 | 5/2013 | LeBoeuf et al. |
| 2013/0316642 A1 | 11/2013 | Newham |
| 2014/0079257 A1 | 3/2014 | Ruwe et al. |
| 2014/0348367 A1 | 11/2014 | Vavrus et al. |
| 2016/0287125 A1 | 10/2016 | Weinberg et al. |

FOREIGN PATENT DOCUMENTS

| | | |
|---|---|---|
| CN | 102365875 B | 9/2014 |
| WO | 2014043179 A3 | 7/2014 |

OTHER PUBLICATIONS

"State Intellectual Property Office of The People's Republic of China", Application No. 201580014988.X, first office action dated Sep. 4, 2018, 8 pages.

European Patent Office, "Office Action", European Patent Application 15 701 341.8, dated Feb. 5, 2019, 6 pages, English translation.

European Patent Office, "Office Action", European Patent Application 15 701 341.8, dated Feb. 5, 2019, 6 pages.

STAND-ALONE MULTIFUNCTIONAL EARPHONE FOR SPORTS ACTIVITIES

PRIORITY STATEMENT

This application is a continuation of U.S. patent application Ser. No. 15/113,435 filed on Jan. 18, 2017 entitled Stand-alone multifunctional earphone for sports activities, which claims priority to PCT Application No. PCT/EP2015/051356 filed on Jan. 23, 2015 entitled Stand-alone multifunctional headphones for sports activities, which claims priority to DE Patent Application 10 2014 100 824.3 filed on Jan. 24, 2014 all of which are hereby incorporated by reference in their entireties.

FIELD OF THE INVENTION

The invention relates to the field of multimedia devices with functionality for acquiring, analyzing and outputting data related to sports activities or medical rehabilitation programs. In particular, the invention relates to the field of portable systems that are suitable for acquiring, analyzing and outputting such data in conjunction with performance of sports activities.

BACKGROUND

There exists a number of different systems which allow users performing sports activities to record and analyze a wide range of different performance relevant and otherwise interesting information, such as for example heart rate, respiratory frequency, velocity, duration and many other data, both during and also after performing the sports activity.

Common to all these systems is that they consist of several parts, for example one or more sensors, such as for example a heart rate monitor strap, and a central unit, such as for example a sports watch, a bicycle computer or a smart phone.

As many users also like to listen to music or radio during their performance of sports activities, the users often has to carry three or more devices, for example a heart rate monitor strap or belt, a bicycle computer, an MP3 player and an earphone.

It is an object of the present invention to provide an apparatus which is capable of providing the functionalities of the numerous hitherto needed devices and which in addition is light and comfortable to wear and carry and easy to operate.

SUMMARY

This object is achieved by the subject matter according to the independent claims. Advantageous embodiments of the present invention are set forth in the dependent claims.

According to a first aspect of the invention, an apparatus is described. The described apparatus comprises the following: (a) a housing configured to be carried in an ear, (b) a motion sensor unit for acquiring motion data, (c) a physiological sensor unit for acquiring physiological data, (d) a data processing unit configured to generate performance data based on the motion data and/or the physiological data, (e) a signal processing unit configured to generate an audio signal based on the generated performance data, and (f) a loudspeaker for outputting the generated audio signal, wherein the motion sensor unit, the physiological sensor unit, the loudspeaker, the data processing unit, and the signal processing unit are incorporated in the housing.

The described apparatus is configured to be carried or worn in the ear and is on its own capable of generating an audio signal and to make the audio signal available to a user by outputting it by means of a loudspeaker, wherein the output audio signal is based on motion data and/or physiological data which is acquired by the sensor units that are incorporated in the housing. Thereby, the user may obtain or receive information in relation to the acquired motion data and/or physiological data without having to connect the apparatus with additional devices. The apparatus thus constitutes an autonomous unit, which may be carried by the user in his or her ear, for example in conjunction with sports activities, and which at the same time may make various information relating to motion or movement and/or physiological parameters available to the user in real-time.

In this document, the term "sensor unit" in particular denotes a unit having one sensor or several individual sensors which are configured to generate one or more electrical signals based on electrical signals from each individual sensor.

In this document, the term "motion sensor unit" in particular denotes a sensor unit which is configured to generate one or more electrical signals in dependency of motion of the sensor unit, in particular electrical signals that depend on an acceleration, a tilt or a displacement of the sensor unit relative to one or more predetermined directions.

In this document, the term "motion data" in particular denotes a digital representation of one or more electrical signals that are generated by the motion sensor unit.

In this document, the term "physiological sensor unit" in particular denotes a sensor unit which is configured to generate one or more electrical signals in dependency of one or more physiological values of a user.

In this document, the term "physiological data" in particular denotes a digital representation of one or more electrical signals that are generated by the physiological sensor unit.

In this document, the term "performance data" in particular denotes data comprising values related to sports activities. Such values in particular comprise values that are descriptive for the sports activity, such as for example the length of a running, driving or swimming route or path, as well as values that are descriptive for the user, such as for example velocity or speed, respiratory rate, oxygen saturation of blood, or heart rate.

The data processing unit is configured to receive and process both the moment data from the motion sensor unit as well as the physiological data from the physiological sensor unit, preferably as digital signals, in order to generate performance data by means of calculations. In this regard, some values of the performance data may be calculated only on the basis of the motion data, other values of the performance data may be calculated only on the basis of the physiological data, and yet further values of the performance data may be calculated on the basis of both the motion data and the physiological data.

The signal processing unit is configured to generate an audio signal based on performance data in such a way that a user hearing the audio signal may perceive or learn about one or more specific values of the performance data, changes in one or more specific values of the performance data and/or a relation between one or more specific values of the performance data and corresponding reference values, in particular threshold values.

The data processing unit and the signal processing unit may be implemented as individual processing units (hardware) or they may be implemented as functional units on one or more processors (software).

The housing, in which the complete apparatus is incorporated, is configured to be carried in the ear of a user. In this regard, the housing is shaped in such a way that the apparatus fits well into a typical ear and such that it can be retained, also during sports activities. The housing may preferably comprise an opening which is shaped and positioned in such a way that the loudspeaker can emit sound into the auditory canal of the user.

Summarizing, the apparatus makes it possible that a user is informed of values of performance data by means of audio output during performance of a sports activity, wherein the individual values of the performance data are based on motion data and/or physiological data which are respectively acquired by the motion sensor unit and the physiological sensor unit during the sports activity.

Thus, the apparatus provides numerous functionalities without any need for additional devices or external sensors. Furthermore, the apparatus is very compact, discrete and pleasant to carry in the ear.

According to an exemplary embodiment of the invention, the motion sensor unit comprises an accelerometer or an acceleration sensor.

The accelerometer is configured to acquire or register acceleration and/or changes in acceleration in at least one predetermined direction relative to the housing. In a preferred embodiment, the accelerometer is a 3D accelerometer, which can register accelerations along three perpendicular directions and which can output three corresponding electrical signals.

By processing the signals from the motion sensor unit, for example by means of pattern recognition, the data processing unit may for example generate the following and further performance data: a number of steps value, a distance value, and a velocity value or pace value.

According to a further exemplary embodiment of the invention, the physiological sensor unit comprises a pulse oximetry sensor or a pulse oximeter, i.e. a sensor for non-invasive determination of arterial oxygen saturation via light absorption measurement.

The pulse oximetry sensor may comprise two differently colored light sources, in particular light emitting diodes, and a photo sensor, and it is preferably arranged in the housing in such a way that the light sources can illuminate a portion of the skin surface in the user's ear and such that the photo sensor can detect corresponding reflections from the skin surface, when the apparatus is positioned in the user's ear. The pulse oximetry sensor may in particular be arranged in a portion of a surface of the housing in such a way that the pulse oximetry sensor is in close contact with the skin surface in the ear, in particular the skin surface in the area behind the tragus, when the apparatus is carried in the ear. (The tragus denotes the small mass of cartilage at the auricle, which is seated just in front of the ear canal (porus acusticus externus)). By driving the light sources and processing the signal output from the photo sensor, the data processing unit may for example, among others, generate the following performance data: an arterial oxygen saturation value, a respiratory frequency value, a cardiovascular flow value, a cardiac output value, a blood pressure value, and a blood glucose value.

According to a further exemplary embodiment of the invention, the audio signal generated by the signal processing unit comprises one or more pre-stored speech elements or tone signals that are indicative of at least one value of the performance data. This means that the speech elements or tone signals acoustically communicate the state and the condition of the carrier, for example by means of tone, pitch, reverb, echo, lingering sound, resonance, three-dimensional perception, or further features.

The generated audio signal may for example consist of a name of a performance parameter followed by the current value of the performance parameter, such as for example "speed" followed by "23 kilometers per hour", "pace" followed by "5 minutes and 17 seconds per kilometer", or "heart rate" followed by "155 beats per minute".

Alternatively, the generated audio signal may consist of a name of the performance parameter followed by a pulsed tone signal, wherein the pulse frequency and/or the pitch of the pulsed tone signal depends on the value of the performance parameter. Thereby, the user may recognize changes in the performance parameter when the pulse frequency and/or the pitch of the tone signal changes.

Further alternatively, the generated audio signal may solely consist of a pulsed tone signal as the one described above.

According to a further exemplary embodiment of the invention, the signal processing unit is configured to modify pre-stored audio data, in particular music, in dependency of at least one value of the performance data.

The modifying of the pre-stored audio data may particularly comprise decreasing or increasing a sound level, a playback speed and/or a tone pitch of the pre-stored audio data in dependency of the at least one value of the performance data. In other words, the signal processing unit may, for example, increase the sound level, the playback speed and/or the tone pitch of the pre-stored audio data, when the heart rate exceeds an upper threshold value, and decrease this/these, when the heart rate deceeds or falls below a lower threshold value.

According to a further exemplary embodiment of the invention, the housing comprises a first portion and a second portion, wherein the first portion is configured to be inserted into an auditory canal and the second portion is configured to be held or retained in an auricle, wherein a shape and/or a size of the second portion is adjustable.

The first portion may be essentially cone-shaped and is formed in such a way that it fits into an outer part of the auditory canal. The loudspeaker may preferably be arranged within the first portion in order to inject sound directly into the auditory canal.

The second portion is formed in such a way that it may be inserted into the concha of the auricle of a typical ear and be retained there. The shape and/or size of the second portion may for example be adjusted by adding self-adhesive material on a part of the surface of the second portion.

The complete housing may in particular be made from plastics. The openings for loudspeaker, sensors etc. may be waterproof sealed such that the apparatus can also be used when swimming.

According to a further exemplary embodiment of the invention, the apparatus further comprises a capacitive sensor unit arranged at a surface of the housing such that it can be touched by a user, when the apparatus is arranged in the user's ear.

The capacitive sensor unit may in particular be arranged on a surface of the housing which points outwards when the apparatus is arranged in the ear.

The capacitive sensor unit is configured to detect touches, in particular tapping or sweeping touches, which the user makes with a finger, for example.

According to a further exemplary embodiment of the invention, the apparatus further comprises a microphone, in particular a bone conduction microphone, which is configured to detect user speech, in particular speech commands spoken by the user.

The use of a bone conduction microphone makes it in particular possible to capture user speech without (or with only insignificant) influence from ambient sounds or noises.

According to a further exemplary embodiment of the invention, the apparatus further comprises an electroencephalography sensor unit (brain current measurement unit) configured to detect an electrical signal at a skin surface of a user.

Predetermined brain activities of the user, in particular personally exciting thoughts, may be detected from the detected electrical signal by means of pattern recognition.

According to a further exemplary embodiment of the invention, the apparatus further comprises a control unit which is integrated in the housing and further configured to control the apparatus in dependency of touches detected by the capacitive sensor unit and/or in dependency of user speech detected by the microphone and/or in dependency of an electric signal detected by the electroencephalography sensor unit.

Thereby, the user may for example control the functionality of the apparatus by touching the capacitive sensor unit, by saying speech commands and/or by thinking predetermined thoughts.

A single short touch (tap) on the capacitive sensor unit may in particular trigger a first control signal; two consecutive short touches may trigger a second control signal, etc. Furthermore, an upward sweep, a downward sweep, a forward sweep, and a rearward sweep may trigger respective predetermined control signals.

According to a further exemplary embodiment of the invention, the apparatus further comprises a contact sensor for detecting whether the apparatus is arranged in the ear.

The contact sensor may in particular be capacitive, and it may be arranged on a part of the housing surface which is in contact with the skin surface when the apparatus is carried in the ear. When the contact sensor has not registered any contact with a skin surface for a period of time, the apparatus may for example be switched into a standby mode or it may be completely switched off.

According to a further exemplary embodiment of the invention, the apparatus further comprises a memory for storing the performance data generated by the data processing unit.

By storing the performance data, these may later on be read out from the memory and processed externally. Furthermore, the stored performance data may be accessed during a sports activity, for example in order to calculate average values or to make comparisons with earlier activities.

According to a further exemplary embodiment of the invention, the apparatus further comprises a communication unit integrated within the housing and configured for wireless communication with an external device.

The communication unit may in particular be a Bluetooth unit by means of which a wireless data communication may be carried out with one or more external devices, such as a mobile phone, a smart phone, a tablet, a laptop computer, etc. Furthermore, a data communication may take place with a further similar or identical apparatus, for example an apparatus that is configured to be carried in the other ear. The communication unit may alternatively be an infrared unit, which enables data transmission with modulated infrared light.

According to a further exemplary embodiment of the invention, the apparatus further comprises a near field communication unit (NFC unit).

The NFC unit allows for storing and/or reading various data in respectively from the apparatus, for example identification data of the user or GPS data, which indicate the last position of the apparatus. Such GPS data may for example be regularly transmitted from a smart phone.

According to a second aspect of the invention, a system is described which comprises two apparatuses according to the first aspect or any of the above exemplary embodiments, wherein both apparatuses are configured for wireless data communication with each other, in particular by means of Bluetooth.

One of the two apparatuses preferably functions as a primary apparatus (master) in the system in the sense that this apparatus transmits control and data signals to the second (secondary) apparatus, wherein in particular sensor signals, which are acquired by the secondary apparatus and transmitted to the primary apparatus, are taken into consideration during the generation of control and data signals in the primary apparatus.

The two apparatuses may output the same audio signal or two different audio signals.

According to an exemplary embodiment of the invention, the signal processing unit of at least one of the two apparatuses is configured to generate a binaural audio signal based on the generated performance data.

In this document, the term "binaural audio signal" in particular denotes an audio signal which, when output into both ears of a user, evokes a spatial hearing impression with precise directional localization. In other words, the user may associate a single component, such as a pulsed tone signal, of a binaural audio signal with a certain position within the three dimensional space.

The binaural audio signal may be used to play or render values in relation to different performance data at different predetermined positions in the three dimensional space around the head of the user, such as for example a first pulsed tone signal or speech signal in relation to a first performance parameter value at a first upper left position and a second pulsed tone signal or speech signal in relation to a second performance parameter value at a second lower front position.

The binaural audio signal may further be used to indicate changes in a performance parameter value relative to a predetermined reference value by changing the playback position. This may for example take place in such a way that the position of a component of the audio signal is shifted upwards or forwards when a performance parameter value exceeds a predetermined reference value or threshold value, wherein the amount of shifting depends on the difference between the performance parameter value and the reference value. The position of the component of the audio signal may in a similar manner be shifted rearwards or downwards when the performance parameter value is below the (or another) reference value or threshold value. Illustratively, this could be implemented in such a manner that a pulsed tone signal in relation to the user's heart rate can be heard at the height or level of the ears when the heart rate is within a predetermined range, such as between 130 and 140 beats per minute, but is shifted upwards when the heart rate exceeds the maximum value of the predetermined range and shifted downwards when the heart rate is below the minimum value of the predetermined range.

According to a further exemplary embodiment of the invention, at least one of the apparatuses comprises a bone conduction microphone and both apparatuses comprise a microphone configured to detect ambient sound.

The bone conduction microphone is in particular configured to acquire speech commands which are spoken by the user in order to control the system. In this regard, the ambient sound acquired by the external microphones can be used for noise reduction in order to improve the recognition of the speech commands. The recognition of the speech commands as well as the processing for the purpose of noise reduction are preferably performed in a corresponding signal processing unit which is integrated into the primary apparatus of the system.

According to a further exemplary embodiment of the invention, at least one of the apparatuses comprises a recognition unit configured to recognize predetermined patterns of motion that emerge from sweeping touches of a bodily surface of a user.

The recognition unit is in particular configured to receive and process a signal from the bone conduction microphone in the primary apparatus and signals from the outwards directed microphones of both apparatuses. The processing in particular comprises an analysis of the timely course of the pitch (frequency) and sound level or intensity for each of the three signals. This processing of the sound signals, which have propagated through respectively around the user's body enables recognition of predetermined patterns of motion, in particular the recognition of a direction of a sweeping touching of the user's body surface. Such recognition is based on the fact that pitch and sound level of the signal acquired by one of the microphones during the motion increases if the motion is directed towards the microphone and decreases if the motion is directed away from the microphone. Thus, an analysis of the signals from the bone conduction microphone allows a determination of whether the motion is directed upwards or downwards. An analysis of the signals from both of the outwards directed microphone allows in a similar manner to determine whether the motion is directed towards the left or towards the right. By means of further analysis of all three signals also inclined or tilted motions can be recognized.

In other words, the recognition unit can recognize when the user for example sweeps a finger from the left to the right or from the top to the bottom of his or her cheek, chest or belly.

The recognition of such patterns of motion or touch can advantageously be used to control the apparatuses or the system. More specifically, each recognizable pattern of motion may be associated with a predetermined control command. An upwards directed movement may for example increase the playback volume and a downwards directed movement may reduce the playback volume.

According to a third aspect of the invention, a method is described. The described method comprises the following steps: (a) acquiring motion data by means of a motion sensor unit, (b) acquiring physiological data by means of a physiological sensor unit, (c) generating performance data based on the motion data and/or the physiological data by means of a data processing unit, (d) generating an audio signal based on the generated performance data by means of a signal processing unit, and (e) outputting the generated audio signal by means of a loudspeaker, wherein the motion sensor unit, the physiological sensor unit, the loudspeaker, the data processing unit, and the signal processing unit are incorporated in a housing that is configured to be carried in the ear.

The described method is essentially based on the same conception idea as the above described apparatus according to the first aspect and the embodiments thereof, namely that motion data and physiological data are acquired and processed in an independent or stand-alone apparatus in order to generate and output an audio signal in dependency of generated performance data.

According to a fourth aspect of the invention, there is described a use of an apparatus according to the first aspect or of a system according to the second aspect or one of the above exemplary embodiments as a headset in conjunction with a mobile communication device, in particular a mobile phone, a smart phone, or a tablet.

The use as headset allows, inter alia, that the various control functionalities of the apparatus, respectively of the system, are employed to control the mobile communications device, and that data, such as GPS data or speech commands from a navigation application or app running on the mobile communications device, are transmitted to the apparatus or system.

The invention may both be realized by means of a computer program, i.e. as software, as well as by means of one or more special electronic circuits, i.e. as hardware, or in any hybrid form, i.e. by means of software components and hardware components.

It is pointed out that embodiments of the invention have been described with reference to different subject matters. In particular, some embodiments of the invention have been described in terms of method claims and other embodiments of the invention have been described in terms of apparatus claims. However, upon reading this application, it will be apparent to the person skilled in the art that, as long as nothing else is explicitly stated, in addition to any combination of features that belong to one type of subject matter, any arbitrary combination of features belonging to different types of subject matter is also possible.

Further advantages and features of the present invention will become apparent from the following exemplary description of a preferred embodiment.

DETAILED DESCRIPTION

Figure 1:
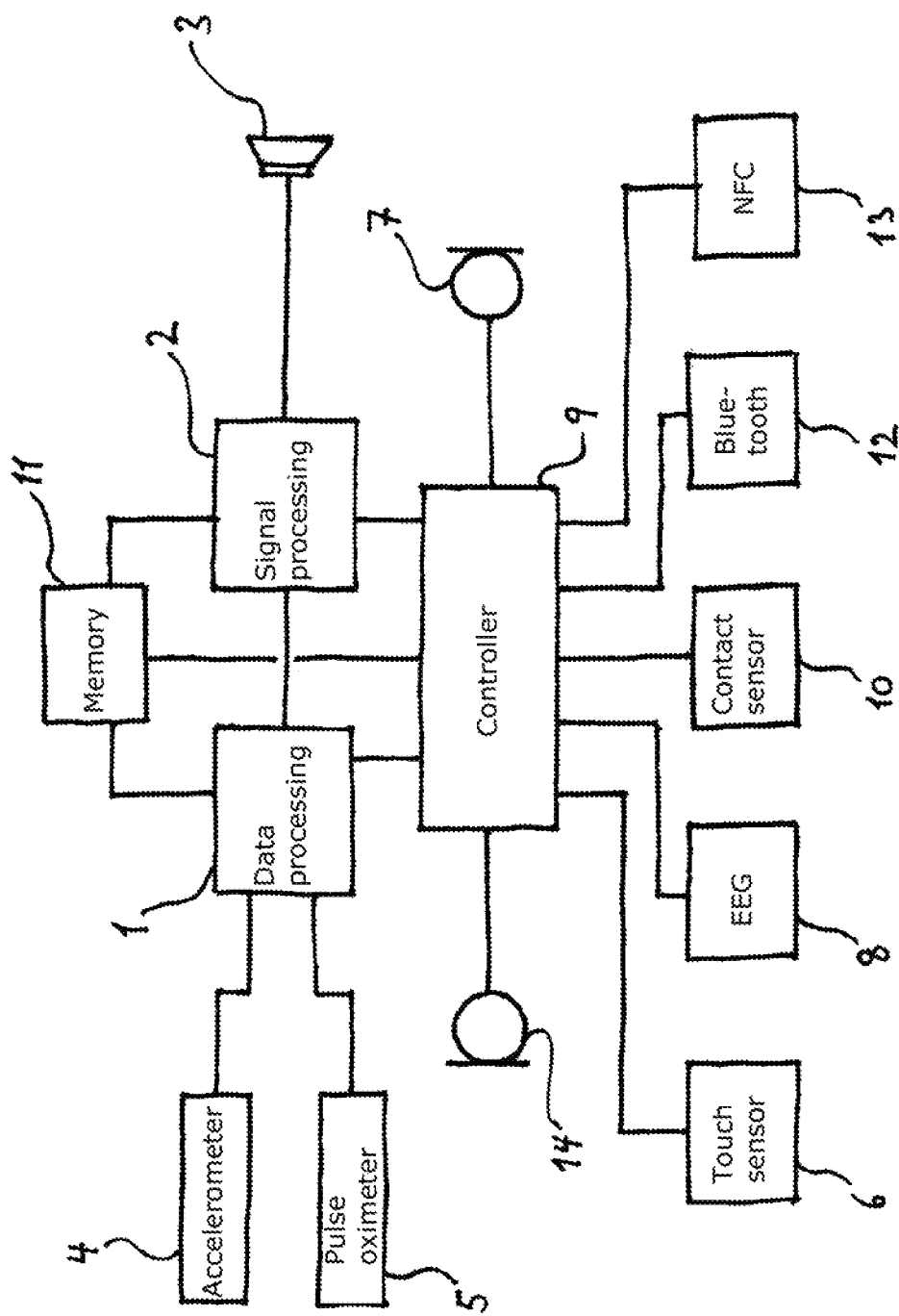
FIG. 1 shows a block diagram of an apparatus according to an exemplary embodiment.

FIG. 1 shows a block diagram of an apparatus according to an exemplary embodiment. The apparatus is incorporated in a housing, which is configured to be carried in the ear and will be described in more detail further below in conjunction with the FIGS. 2A, 2B and 2C. The apparatus comprises a data processing unit 1, a signal processing unit 2, a loudspeaker or receiver 3, an accelerometer 4 and a pulse oximeter or a pulse oximetry sensor 5.

The data processing unit 1 receives data from the accelerometer 4 and the pulse oximeter 5 and processes these in order to generate or calculate performance data, such as for example a number of steps, a distance, a speed, an arterial oxygen saturation, a respiratory frequency, a cardiovascular flow, a cardiac output, a blood pressure, a blood glucose value, etc. The performance data are communicated to the signal processing unit 2 and used by the signal processing unit 2 to generate an audio signal, which is output into the ear of the user by means of the loudspeaker 3. The audio signal is generated in such a way that the user, when hearing the corresponding sound, can learn information about at least one value of the performance data. This may take place by outputting speech elements (for example pre-stored numbers and words) or pulsed tone signals, by manipulating music or in any other suitable way.

The apparatus further comprises a central control unit or controller 9 and a memory 11. The controller 9 is connected with the data processing unit 1, with the signal processing unit 2 and with the memory 11, and is configured to control these units and to receive or read out information from these units. For example, the controller 9 controls which of the performance data generated by the data processing unit 1 the signal processing unit 2 shall take into consideration when generating the audio signal, for example whether the audio signal is currently to provide information on heart rate, speed or something else. The controller 9 can also control the signal processing unit 2 in such a way that music or the like (for example an audio book) is played back independently of the performance data.

The controller 9 is furthermore connected with a first microphone 7, with a second microphone 14, with a touch sensor unit 6, with an EEG unit (electroencephalography unit) 8, with a contact sensor unit 10, with a Bluetooth unit 12, and with an NFC unit (Near Field Communication unit) 13. These units are also incorporated or integrated in the housing and generally enable the user to influence and control the functionalities of the apparatus and also allow the apparatus to communicate with an external device, such as for example a similar apparatus, a smart phone or a computing device.

The first microphone 7 is a bone conduction microphone which is arranged in the housing in such a way that it can detect sound being conducted through the cranial bone, for example while speaking. One function of the first microphone 7 is to detect user speech, for example speech commands for controlling the apparatus, or when the apparatus is used as a headset in conjunction with an external device.

The second microphone 14 is arranged in the housing in such a way that it may in particular detect ambient sound. By processing the signals from both the first microphone 7 and the second microphone 14, disturbing ambient noises can be filtered out of the user speech, which improves the use as a headset as well as the quality of recognition of speech commands. A further use of the two microphone signals is the recognition of acoustic gestures, i.e. the recognition of certain moving or sweeping touches of the body surface. More specifically, an acoustic gesture may for example consist in the user making a rapid sweeping movement with a finger across his or her skin or clothes in a particular direction (vertically, horizontally, etc.), wherein the finger touches the skin or clothes during the entire movement. Sound emerges from such sweeping movements and by analyzing the signals recorded by the microphones 7 and 14, the direction, speed and further characteristics of the gesture can be recognized and converted into control signals.

The touch sensor unit 6 comprises a plate with a plurality of capacitive sensors and is arranged on a part of the surface of the housing in such a way that the user can touch it with the finger when the apparatus is carried in the ear. In other words, the touch sensor unit 6 is located on a surface of the housing pointing away from the auditory canal. The user can control the apparatus by sweeping and/or tapping with the finger on the touch sensor unit 6. For example, the control unit 9 may link a sweeping upward movement with a sound level increase and a sweeping downward movement with a sound level decrease and control the signal processing unit 2 accordingly. In a similar manner, the control unit 9 may for example link a single tap on the touch sensor unit 6 with a change of function and it may link two recurring taps with a selection of a function.

The EEG unit 8 comprises a plurality of electrodes arranged on the surface of the housing in such a way that measurements of electric potentials can be carried out on the skin surface in the ear. These measurements are analyzed by the control unit and compared with pre-stored measurements in order to recognize particular thoughts of the user and to use these as control commands. Thinking intensively of one's own favorite dish may for example trigger an announcement of the present calorie consumption.

The contact sensor unit 10 comprises a capacitive sensor arranged in the surface region of the housing in such a way that it contacts the skin surface of the user when carried in the ear. Thus, the controller 9 can detect whether the apparatus is in use or not and in accordance therewith generate different control signals. For example, functionalities with intensive current consumption may be shut off a couple of minutes after the apparatus has been taken out of the ear.

The Bluetooth unit 12 serves to provide wireless communication with other devices (for example an apparatus carried in the other ear) or with external devices (mobile phone, PC, etc.). When communicating with an apparatus in the other ear of the user, sensor signals from both sides may be taken into consideration in order to obtain an improved precision in the performance data. Furthermore, the generated audio signal may be stereophonically or binaurally processed. In such systems, one apparatus functions as a primary apparatus or master in the sense that it receives and processes data from both apparatuses and defines the respective audio signals that are to be output.

Communication with an external device may take place during use of the apparatus, i.e. during performance of a sports activity. In this case, data, such as music or GPS data, may be transmitted from the external device to the apparatus and used or stored therein. At the same time, data, such as acquired sensor data or calculated performance data, may be transmitted from the apparatus to the external device. This also enables a use of the apparatus as headset in conjunction with communication applications.

Communication with the external device may also take place when the apparatus is not used in the ear, for example in order to configure the different control options described above, in order to set threshold values (for example for heart rate, respiratory rate, distance, time or speed, etc.) or in order to read out performance data for external processing. This is conveniently done by means of a special application or app.

The NFC unit 13 makes it possible to communicate with an NFC enabled device, for example a smart phone, when this is brought into the vicinity of the apparatus. Thereby, configuration data can be transferred from the smart phone to the apparatus or data stored in the apparatus, such as for example the user's contact information, can be read out. This information can be of use when a lost apparatus is found or in case of an accident.

Figure 2A:
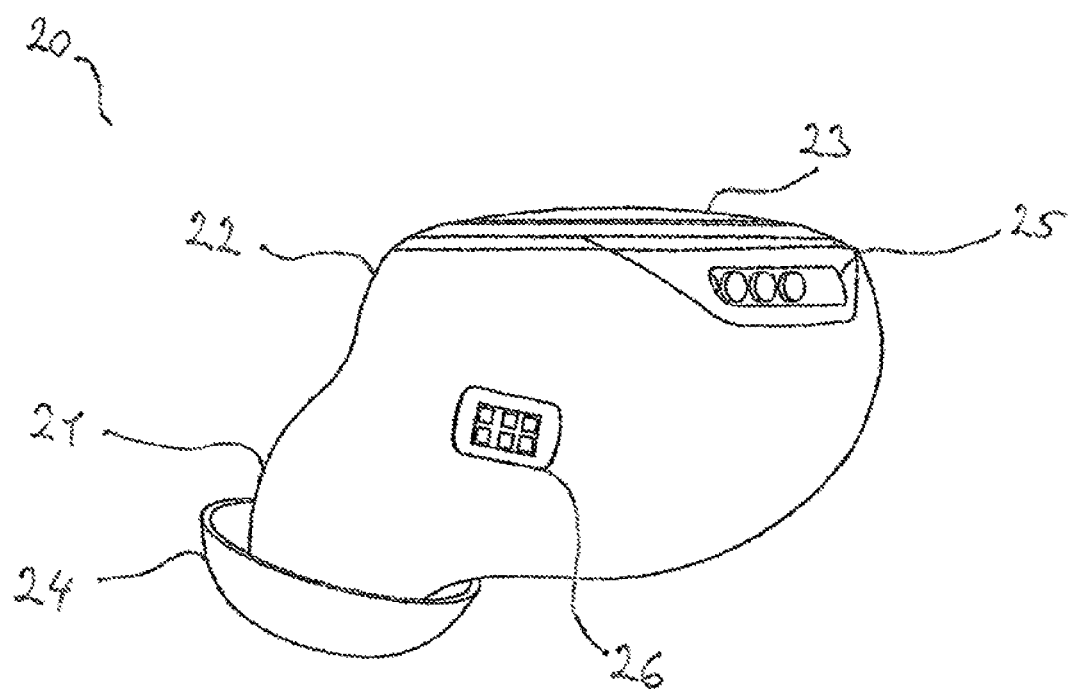
FIG. 2A shows a first view of an apparatus according to an exemplary embodiment.
Figure 2B:
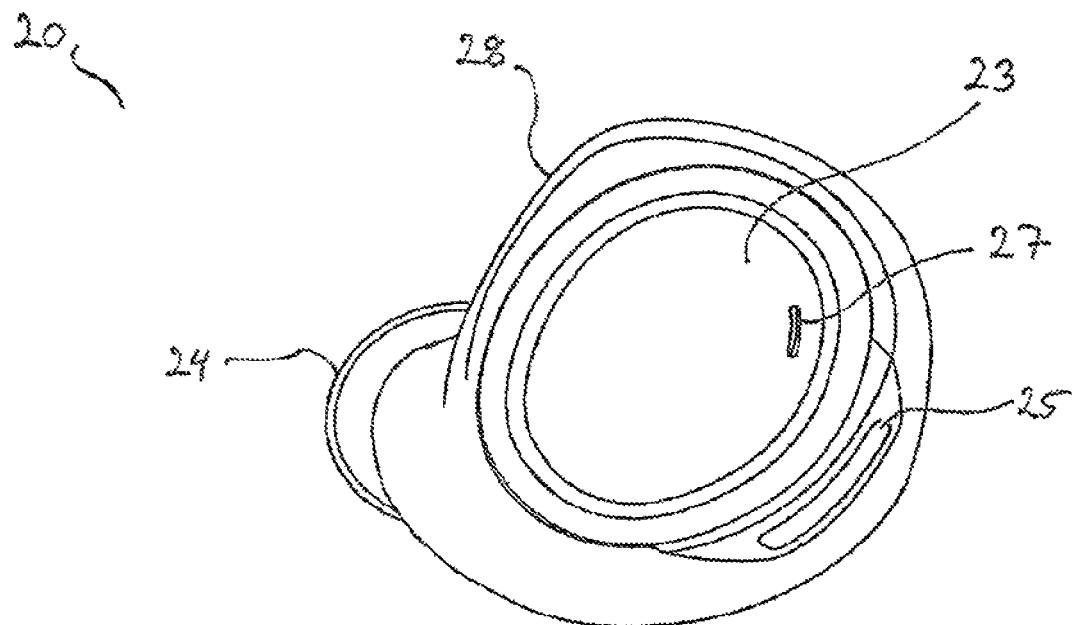
FIG. 2B shows a second view of an apparatus according to an exemplary embodiment.
Figure 2C:
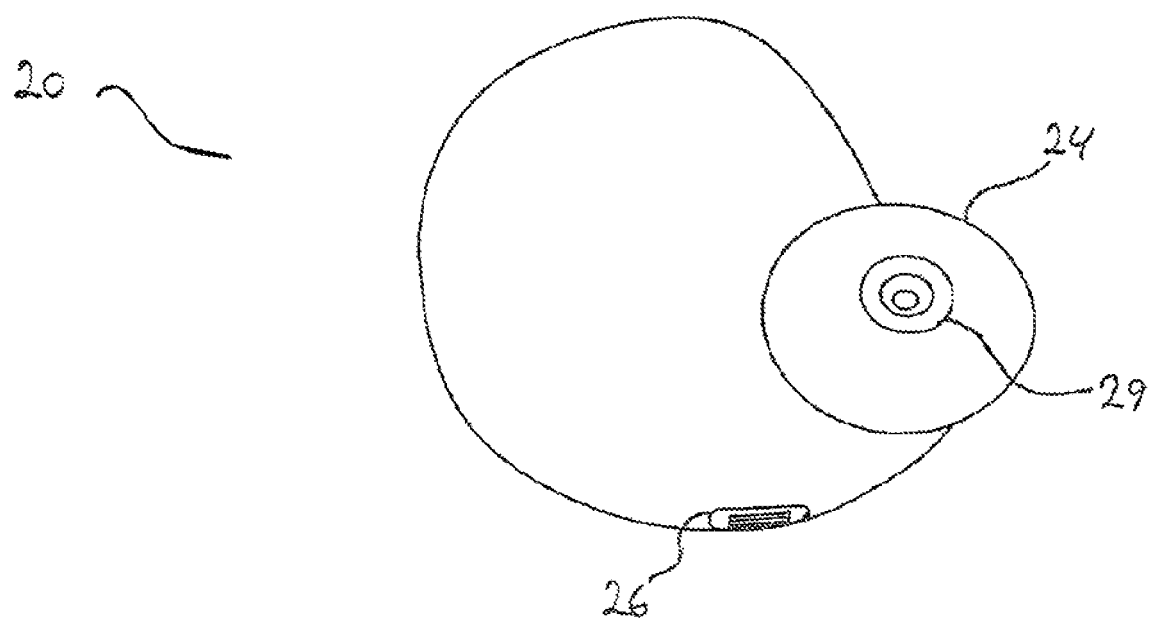
FIG. 2C shows a third view of an apparatus according to an exemplary embodiment.

The FIGS. 2A, 2B and 2C show different views of an apparatus 20 according to an exemplary embodiment, in particular they show the shape of the housing into which all units of the apparatus 20 are incorporated.

FIG. 2A shows a view of an apparatus 20, which comprises a housing. The housing is made of plastics or synthetic material, such as silicone, and essentially comprises a first portion 21 and a second portion 22. The first portion 21 is shaped to be inserted into the auditory canal of a user and the second portion 22 is shaped to be retained in the user's auricle or outer ear. In this regard, the first portion 21 is essentially cone-shaped in order to fit well into the outer section of the auditory canal. An elastic collar 24 is provided at an end section of the first portion 21. The collar 24 functions as a seal when the apparatus 20 is carried in the ear so that the apparatus 20 blocks the user's auditory canal. The second portion 22 is shaped in such a way that it can be inserted into the concha of the auricle of a typical ear and such that it can be retained there.

The housing further comprises a surface 23 which points away from the auditory canal and thus can be reached by the user, for example with a finger. The surface 23 particularly comprises a capacitive sensor unit for acquiring control commands from the user, for example when the user taps with his or her finger on the surface 23 or when the user swipes a finger across the surface 23 in a predetermined direction. The housing comprises a closable opening 25 in the vicinity of the surface 23 through which a (not shown) plug can be coupled to a socket in order to charge the battery of the apparatus 20 or in order to exchange data with the apparatus 20.

The housing further comprises an opening 26 located at a position of the surface of the housing which closely contacts the skin, in particular in the area behind the tragus, when the apparatus 20 is carried in the ear. The opening 26 may comprise a pulse oximetry sensor having two differently colored light sources, in particular light emitting diodes, and a photo sensor. In this case, the opening 26 is positioned in the housing in such a way that the light sources can illuminate a portion of the skin surface in the user's ear and such that the photo sensor can detect corresponding reflections from the skin surface. Alternatively, the opening 26 may contain a bone conduction microphone. In a system comprising two apparatuses, one apparatus may comprise the pulse oximetry sensor and the other apparatus may contain the bone conduction microphone.

FIG. 2B shows a further view of the apparatus 20, wherein the surface 23 can be seen in the foreground. The surface 23 comprises a slot- or slit-shaped opening 27 which lets sound originating from the surroundings through to a (not shown) microphone. The apparatus 20 further comprises a cuff or sleeve 28, which surrounds a part of the surface 23 and serves to adapt the size of the apparatus to the ear of a user. The cuff 28 is made from soft plastics and is detachable from the housing. Thereby, the user may try different sleeves 28 having different sizes and choose the one that provides the best fit.

FIG. 2C shows a yet further view of the apparatus 20, wherein the apparatus 20 is turned 180° in comparison to the view of FIG. 2B. Both the collar 24 and also the end of the first portion 21, which extends deepest into the auditory canal, comprise openings 29 through which the sound that is generated by a loudspeaker which is incorporated in the apparatus can be output.

The openings 25, 26, 27 and 29 are all waterproof sealed so that the apparatus 20 can also be used for swimming or when it rains.

What is claimed is:

1. An apparatus comprising:
   a housing configured to be carried in an ear,
   a motion sensor unit configured to detect motion data, wherein the motion sensor unit is comprised of at least one accelerometer;
   a physiological sensor unit configured to detect physiological data, wherein the physiological sensor comprises at least one pulse oximeter;
   a data processing unit configured to receive motion data from the motion sensor unit and physiological data from the physiological sensor unit and generate performance data based on the motion data and the physiological data, wherein the data processing unit is operatively connected to the motion sensor unit and the physiological sensor unit;
   a signal processing unit operatively connected to the data processing unit configured to generate a binaural audio signal with a first component at a first location in 3D space relative to a user of the apparatus based on the performance data and a second component at a second location in 3D space relative to the user based on the performance data, wherein the performance data includes at least one of a value indicative of distance, speed, respiratory rate, oxygen saturation, heart rate, pace, or number of steps; and
   a loudspeaker for outputting the generated first audio signal at the first location and the second audio signal at the second location;
   wherein the motion sensor unit, the physiological sensor unit, the loudspeaker, the data processing unit, and the signal processing unit are incorporated in the housing;
   wherein the generated performance data comprises a first parameter value and a second parameter value;
   wherein the first component of the binaural audio signal is based on the first parameter value of the generated performance data;
   wherein the second component of the binaural audio signal is based on the second parameter of the generated performance data.

2. The apparatus according to claim 1, wherein the first component comprises a speech element.

3. The apparatus according to claim 1, wherein the signal processing unit is configured to modify pre-stored audio data using the performance data.

4. The apparatus according to claim 1, wherein the housing comprises a first portion and a second portion, wherein the first portion is configured to be inserted into an auditory canal and the second portion is configured to be held in an auricle, wherein a shape and/or a size of the second portion is adjustable.

5. The apparatus according to claim 1, further comprising a touch sensor unit comprising at least one capacitive sensor arranged at a surface of the housing such that it can be touched by a user, when the apparatus is arranged in the user's ear.

6. The apparatus according to claim 5, further comprising a controller which is integrated in the housing and further configured to control the apparatus in dependency of touches detected by the touch sensor unit wherein the controller is operatively connected to the touch sensor unit.

7. The apparatus according to claim 1, further comprising a microphone which is configured to detect user speech.

8. The apparatus according to claim 7, further comprising a controller which is integrated in the housing, operatively connected to the microphone, and further configured to control the apparatus in dependency of user speech detected by the microphone.

9. The apparatus according to claim 1, further comprising a contact sensor for detecting whether the apparatus is arranged in the ear.

10. The apparatus according to claim 1, further comprising a memory for storing the performance data generated by the data processing unit.

11. The apparatus according to claim 1, further comprising a communication unit integrated within the housing and configured for wireless communication with an external device.

12. The apparatus according to claim 1, further comprising a near field communication unit.

13. A system comprising two apparatuses according to claim 1, wherein both apparatuses are configured for wireless data communication with each other.

14. The system according to claim 13, wherein the signal processing unit of at least one of the two apparatuses is configured to generate the binaural audio signal based on the generated performance data.

15. The system according to claim 14, wherein at least one of the apparatuses comprises a bone conduction microphone and wherein both apparatuses comprise a microphone configured to detect ambient sounds.

16. The system according to claim 15, wherein at least one of the apparatuses comprises a recognition unit configured to receive and process the ambient sounds to recognize predetermined patterns of motion that emerge from sweeping touches of a bodily surface of a user.

17. The apparatus according to claim 1, further comprising an electroencephalography sensor unit comprising at least one electrode configured to detect an electrical signal at a surface of the skin of a user, and a controller which is integrated in the housing and further configured to control the apparatus in dependency of an electric signal detected by the electroencephalography sensor unit, wherein the controller is operatively connected to the electroencephalography sensor unit.

\* \* \* \* \*